United States Patent [19]

Frech et al.

[11] 3,953,511

[45] Apr. 27, 1976

[54] PREPARATION OF 2-METHYL-1,5-DIAMINOPENTANE

[75] Inventors: Kenneth J. Frech, Tallmadge; Lawson G. Wideman, Akron, both of Ohio

[73] Assignee: The Goodyear Tire & Rubber Company, Akron, Ohio

[22] Filed: Nov. 4, 1974

[21] Appl. No.: 520,517

[52] U.S. Cl. .................. 260/583 K; 260/465.8 R; 260/583 P; 260/683.9; 252/477 Q
[51] Int. Cl.² .................. C07C 85/11; C07C 87/14
[58] Field of Search .............. 260/583 K, 465.8 R, 260/683.9, 583 P

[56] References Cited
UNITED STATES PATENTS

| | | | |
|---|---|---|---|
| 3,350,455 | 10/1967 | White et al. | 260/583 K |
| 3,408,397 | 10/1968 | Feldman et al. | 260/583 K |

OTHER PUBLICATIONS

Lieber et al., in Advances in Catalysis, Vol. 5 (1953), Academic Press, NY; N. Y., pp. 424–425.

*Primary Examiner*—Arthur P. Demers
*Attorney, Agent, or Firm*—F. W. Brunner; J. Y. Clowney

[57] ABSTRACT

There is disclosed a process for the preparation of 2-methyl-1,5-diaminopentane by a multi-stage hydrogenation of α-methylene glutaronitrile using as a catalyst a highly dispersed form of nickel in which the first stage hydrogenation is conducted at temperatures ranging from about 20°C to about 50°C and a hydrogen pressure of at least about 14 kilograms per square centimeter and the second stage hydrogenation is conducted at temperatures ranging from about 120°C to about 140°C using a hydrogen pressure of at least about 42 kilograms per square centimeter.

2 Claims, No Drawings

PREPARATION OF 2-METHYL-1,5-DIAMINOPENTANE

This invention is directed to the preparation of 2-methyl-1,5-diaminopentane. More specifically, it is directed to the preparation of 2-methyl-1,5-diaminopentane by a multi-stage hydrogenation process of α-methylene glutaronitrile using as a single catalyst a highly dispersed form of nickel metal such as Raney nickel.

The preparation of 2-methyl-1,5-diaminopentane from α-methylene glutaronitrile is not new. In French patent specification 1,482,577, there is disclosed a process whereby 2-methyl-1,5-diaminopentane is prepared from α-methylene glutaronitrile by a multi-stage hydrogenation process. This prior art process uses in the first stage hydrogenation, a catalyst which is 5 percent palladium on carbon. After the first stage hydrogenation is complete this catalyst is subsequently removed from the hydrogenation mixture and a second catalyst, a Raney cobalt, is employed in the second stage hydrogenation to give 2-methyl-1,5-diaminopentane. In the first stage hydrogenation, the temperature employed was 22°C and a hydrogen pressure of about 103.33 kilograms per square centimeter (kg/cm$^2$) (100 atmospheres) was used. In the second stage hydrogenation, the temperature employed was about 100°C and the hydrogen pressure was about 377 kg/cm$^2$.

The present invention provides a process whereby only one catalyst system is employed for both the first and second stage hydrogenations, thereby avoiding the disadvantage of removing the first stage hydrogenation catalyst from the mixture and adding another catalyst before the second stage hydrogenation is accomplished.

Thus, the invention is a method for the preparation of 2-methyl-1,5-diaminopentane by a multi-stage hydrogenation of α-methylene glutaronitrile employing as a catalyst a highly dispersed nickel metal, in which the first stage hydrogenation is conducted at temperatures ranging from about 20° to about 50°C and a hydrogen pressure of at least about 14 kg/cm$^2$ and wherein the second stage hydrogenation is conducted at temperatures ranging from about 120°C to about 140°C using a hydrogen pressure of at least about 42 kg/cm$^2$.

In the first stage hydrogenation of the process of this invention, the α-methylene glutaronitrile is believed to be converted to α-methyl glutaronitrile, by conversion of the methylene group to the methyl group, and in the second stage hydrogenation the α-methyl glutaronitrile is converted to 2-methyl-1,5-diaminopentane, by conversion of the nitrogens to amino groups.

These reactions can be set forth as:

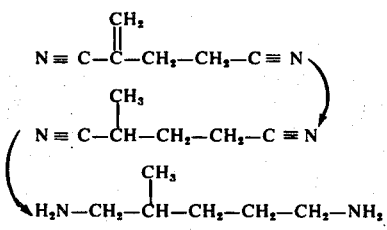

The temperature at which the various stages of hydrogenation are conducted have been found to be somewhat critical. In the first stage hydrogenation, wherein the methylene group is converted to a methyl group, the temperature must be controlled from slightly below room temperature to about 50°C. If the temperature is allowed to rise above about 50°C, the α-methylene glutaronitrile tends to polymerize to form a polymeric material which is undesirable. The first stage reduction of the methylene group to the methyl group is accomplished by controlling the temperature in a range from about 20°C to about 50°C and the hydrogen pressure to at least 42 kg/cm$^2$. The first stage hydrogenation is controlled under these conditions until the hydrogen uptake ceases when one realizes the methylene group has been converted to a methyl group. At that time, the temperature is raised to the range of about 120°C to about 140°C and the hydrogen pressure is increased to at least about 42 kg/cm$^2$. In the second stage hydrogenation, the nitrile groups of the α-methyl glutaronitrile are converted into amino groups to form the 2-methyl-1,5-diaminopentane.

It has been found that the process is best conducted in a solvent system. A variety of solvents may be employed in the process of this invention. The hydrocarbon solvents such as benzene, pentane and hexane are less preferred because of the poor solubility of α-methylene glutaronitrile in non-polar solvents. An alcohol is the solvent of choice with ethanol being most preferred. The ratio of solvent to α-methylene glutaronitrile should not be too great since it has been observed that a large amount of low boiling by-products are formed at high solvent to reactant ratios. For instance, 20 grams of α-methylene glutaronitrile made up to 400 milliliters volume in ethanol will give an appreciable amount of what is presumably an ethanolic by-product. Similarly, higher boiling by-products will be formed if too little solvent is employed. For instance, if 100 grams of α-methylene glutaronitrile is made up to 200 milliliters volume with ethanol, a high yield of high boiling by-products is formed in the first stage hydrogenation. Therefore, the solvent to α-methylene glutaronitrile weight ratio should vary between about 1/1 to about 3/1.

While it is possible to conduct the hydrogenations of this invention using the α-methylene glutaronitrile (MGN) in the solvent in the absence of any tertiary amine, ammonia or other basic materials, it is preferred to employ small amounts of such materials in the system. The use of these basic materials tends to suppress the formation of secondary and/or heavier amines during the hydrogenations. The amount of the basic material employed depends on the particular one chosen. If an amine is used, large excess of the amine based on the reactant may be used, up to about a weight ratio of amine to MGN of 6/1. If ammonia, the preferred basic material, is employed, the amounts found to be satisfactory would range up to a saturated solution of ammonia in the solvent and MGN at about room temperature. If a large excess of ammonia is used, this excess leads to extremely high pressures being developed during the second stage hydrogenation at the higher temperatures therein employed.

Thus, it is usually desirable to conduct the process of the invention in an alcoholic solvent which has been made basic by saturating the alcohol solvent/α-methylene glutaronitrile mixture with ammonia.

The pressure of the hydrogen employed in both the first and second stage hydrogenation has not been found to be as critical as the temperatures. No upper limit on the hydrogen pressure of either the first or second stage hydrogenation has been determined. It has been observed however that at least 14 kg/cm² hydrogen pressure should be employed in the first stage hydrogenation. However, due to the exothermic nature of the initial hydrogenation reaction, an excessive hydrogen pressure, ie, above about 28 kg/cm², would be a waste. In the second stage hydrogenation, the autogenous vapor pressure, which is in the neighborhood of 31 kg/cm², of the reaction which is conducted at temperatures from about 120°C to about 140°C forces a lower constraint on the hydrogen pressure. Thus, a hydrogen pressure of less than about 35 kg/cm² tends to give inferior results. Therefore, a preferred hydrogen pressure of at least 42 kg/cm² is required in the second stage hydrogenation.

The catalyst employed in both the first and second stage hydrogenation of α-methylene glutaronitrile of this invention is a highly dispersed form of nickel. Raney nickel has been found to be a very good form of highly dispersed nickel for use in the invention. The methods of preparing the Raney nickel catalysts which are useful in this invention are known and can be found in a book entitled "Catalytic Hydrogenation" by Robert L. Augstine published in 1965 by Marcel Dekker, Inc, New York, NY. The procedures employed to prepared Raney nickel do not vary widely and are given in the text above. The author refers to these Raney nickel catalysts as W1, W2, W3, W4, W5, W6, W7 and W8. In addition to the W-type Raney nickel, a Raney nickel referred to as T-1 is preferred or a modification of T-1 Raney nickel is preferred.

In the Journal of Organic Chemistry 26, 1625 (1961), there is described a process for the preparation of what the authors refer to as T-1 Raney nickel by Dominguez, Lopez and Franco. In this article, the authors state that the preparation of the T-1 Raney nickel catalyst is a modification of the procedure described by Papa, Schwenk and Whitman in the Journal of Organic Chemistry 7, 586, (1942) and Papa, Schwenk and Brieger in the Journal of Organic Chemistry 14, 366 (1949). All of the Raney nickels described in the articles referred to above are operable in the process of this invention.

Other nickel catalysts useful in the invention can be obtained by the use of new techniques known to the catalyst art for depositing metals on suitable supports in a highly dispersed form. These nickel catalysts would exhibit catalytic properties similar to the properties exhibited by the Raney nickel catalysts.

In the article by Dominguez et al., the authors state that the T-1 Raney nickel is prepared as follows.

In a 1-liter, 3-neck flask containing 600 ml of a 10 percent sodium hydroxide solution, 40 grams of Raney nickel aluminum alloy (50 percent nickel) was added in small portions over a period of 20 to 30 minutes with mechanical stirring. The temperature being kept during this addition at 90°–95°C. The mixture was stirred for an additional hour period at which time the stirring was stopped and the nickel was allowed to settle, and the solution decanted. The reduction was washed with five 200 ml portions of water and then 5 times with 50 ml of ethanol in such a manner that the nickel was always covered with liquid. The catalyst was then stored under ethanol and refrigerated for further use.

The Raney nickel actually employed in the examples of this application, and termed by the present inventors as Modified T-1 Raney nickel, was prepared by a slight modification of Dominguez et al's procedure and is as follows:

A solution of 6 grams of sodium hydroxide in 50 ml of water was heated to its boiling point and then there was added 6 grams of Raney nickel aluminum alloy (3 grams of Raney nickel) as rapidly as the hydrogen evolution permits. This mixture was then digested at 95° to 100°C for 1 hour (reflux) and the water was continually replaced as it evaporated. The solution was decanted from the Raney nickel and the metal washed with three 250 ml portions of cold water. This catalyst was employed without further washing with additional ethanol.

The ratio of catalyst to the α-methylene glutaronitrile has not been accurately determined but less than 1 part by weight of catalyst per 100 parts of α-methylene glutaronitrile leads to inferior results and a catalyst to reactant ratio greater than 4 parts by weight of Raney nickel to 100 parts of α-methylene glutaronitrile has not been found to be required. Thus, it could be stated that from 1 part by weight of nickel up to 4 parts by weight per 100 parts by weight of α-methylene glutaronitrile could be employed.

The invention is further illustrated by reference to the following examples which are intended to be representative in nature and in no way limiting of the invention.

EXAMPLE I

A heat dried, 1-liter stainless steel reactor was flushed with nitrogen and charged with an ethanolic solution (200 ml total volume) containing 50 g of α-methylene glutaronitrile and saturated with anhydrous ammonia (ca. 10 g). The solution contained a suspension of 3 g of the modified T-1 Raney nickel catalyst. The reactor was then charged with about 28 kg/cm² of hydrogen at room temperature and the contents of the reactor were stirred continuously. The hydrogen pressure was maintained at about 28 kg/cm² and the temperature was not allowed to rise above 45°C by employing cooling coils within the reactor. The uptake of hydrogen usually ceased after about 15 minutes. The temperature was then raised to 120°C and the hydrogen pressure was raised and maintained at about 42 kg/cm² for 3 hours. The hydrogen pressure was maintained as it was consumed. The reactor and its contents were then cooled to room temperature. The catalyst was filtered from the reaction mixture. Gas chromatographic analysis of the reaction mixture on a 50' UCW-98 column (programmed from 80°C to 240°C) revealed a quantitative conversion of α-methylene glutaronitrile. The selectivity of 2-methyl-1,5-diaminopentane was 62% and the selectivity to 3-methylpiperidine was 21%, with 14% selectivity to amino-nitrile, which can be recycled to produce more 2-methyl-1,5-diaminopentane.

The 2-methyl-1,5-diaminopentane was removed by distillation in the following manner. The ethanol and 3-methylpiperidine were flashed away from the reaction mixture at atmospheric pressure; the crude 2-methyl-1,5-diaminopentane was then distilled from heavies by reducing the pressure to about 1 mm and applying a small amount of heat (the heavies tend to pyrolyze and liberate ammonia when attempts are made to distill the 2-methyl-1,5-diaminopentane at atmospheric pressure). When the diaminopentane has been removed from the heavies, it is redistilled at atmospheric pressure to give a water-white liquid (bp 192°–195°C).

EXAMPLE II

A reaction was carried out under the conditions of Example I, except that the reaction time at 120°C was 4½ hours. Gas chromatographic analysis revealed a quantitative conversion of α-methylene glutaronitrile and a 41% selectivity to 2-methyl-1,5-diaminopentane and a 55% selectivity to 3-methylpiperidine, with a 3% selectivity to an amino-nitrile.

EXAMPLE III

A reaction was carried out under the conditions of Example I, except that the reaction time at 120°C was 2½ hours. Gas chromatographic analysis revealed a quantitative conversion of α-methylene glutaronitrile and a 60% selectivity to 2-methyl-1,5-diaminopentane.

EXAMPLE IV

A reaction was carried out under the conditions of Example I, except that the reaction temperature was held at 110°C for 1½ hours. Gas chromatographic analysis revealed a quantitative conversion of α-methylene glutaronitrile and a 54% selectivity to 2-methyl-1,5-diaminopentane.

EXAMPLE V

A reaction was carried out under the conditions of Example I, except that the reaction temperature was 150°C for 1½ hours. Gas chromatographic analysis revealed a quantitative conversion of α-methylene glutaronitrile and a 46% selectivity to 2-methyl-1,5-diaminopentane.

While certain respresentative embodiments and details have been shown for the purpose of illustrating this invention, it will be apparent to those having skill in this art that certain changes and modifications may be made therein without departing from the spirit or scope of the invention.

What is claimed is:

1. The method for the preparation of 2-methyl-1,5-diaminopentane which comprises hydrogenating α-methylene glutaronitrile in a multi-stage hydrogenation employing as the hydrogenation catalyst in both hydrogenation stages T-1 Raney nickel or modified T-1 Raney nickel wherein the first stage hydrogenation is conducted at a temperature ranging from about 20°C to about 50°C and at a hydrogen pressure of at least about 14 kg/cm$^2$ and wherein the second stage hydrogenation is conducted at temperatures ranging from about 120°C to about 140°C and a hydrogen pressure of at least about 42 kg/cm$^2$.

2. The method according to claim 1 in which the hydrogenations are conducted in an ethanolic solvent solution containing ammonia.

\* \* \* \* \*